(12) United States Patent
Hocking

(10) Patent No.: US 12,667,285 B2
(45) Date of Patent: Jun. 30, 2026

(54) GENERALIZED PULSE OXIMETRY METHOD FOR PERSONS OF ALL SKIN PIGMENTATIONS

(71) Applicant: Grant Hocking, Alpharetta, GA (US)

(72) Inventor: Grant Hocking, Alpharetta, GA (US)

(73) Assignee: KardiaMetrix LLC, Alpharetta, GA (US)

( * ) Notice: Subject to any disclaimer, the term of this patent is extended or adjusted under 35 U.S.C. 154(b) by 386 days.

(21) Appl. No.: 18/175,711

(22) Filed: Feb. 28, 2023

(65) Prior Publication Data

US 2023/0284942 A1 Sep. 14, 2023

Related U.S. Application Data

(60) Provisional application No. 63/319,463, filed on Mar. 14, 2022.

(51) Int. Cl.
*A61B 5/1455* (2006.01)
*A61B 5/00* (2006.01)
*A61B 5/145* (2006.01)

(52) U.S. Cl.
CPC ...... *A61B 5/14552* (2013.01); *A61B 5/14546* (2013.01); *A61B 5/721* (2013.01); *A61B 5/7246* (2013.01); *A61B 2562/0233* (2013.01)

(58) Field of Classification Search
CPC . A61B 5/14552; A61B 5/14546; A61B 5/721; A61B 5/7246; A61B 2562/0233; A61B 5/14551
See application file for complete search history.

(56) References Cited

U.S. PATENT DOCUMENTS 5,309,907 A * 5/1994 Fang .................... A61B 5/0073
600/476
6,070,092 A 5/2000 Kazama
(Continued)

FOREIGN PATENT DOCUMENTS

CN 112858196 5/2021

OTHER PUBLICATIONS

The International Search Report/Written Opinion released in corresponding PCT application No. PCT/US2023/063392 on Aug. 23, 2023; 10 pages.
(Continued)

*Primary Examiner* — Abid A Mustansir
(74) *Attorney, Agent, or Firm* — Smith Gambrell & Russell LLP

(57) ABSTRACT

The present invention is an in vivo non-invasive method and apparatus for the measurement of the arterial blood oxygen saturation status of a patient, the method is a generalized improvement on conventional pulse oximetry to correct for its skin pigmentation bias and significant errors in oxygen saturation assessment in the presence of methemoglobin. The method requires an additional red light sensor with an infrared long pass filter to conventional pulse oximetry, and utilizes red and infrared light and sensors to non-invasively measure the peripheral pulse optical plethysmograph waveforms (PPG) at three light wavelengths, red, long pass red and infrared, positioned over a finger, or ear or other extremity, and from the pulse oximetric ratio of ratios transforms the PPG measurements by a processing device that determines the subject's arterial blood oxygen saturation directly, without the need for an empirical correction as is required in conventional pulse oximetry. The method determines the red transmitted light waveform and thus quantifies the wavelength shift from the incident red light (Continued)

due to the subject's skin pigmentation, and from in vivo hemoglobin extinction coefficients, determines the relative concentrations of oxygenated and deoxygenated hemoglobin and methemoglobin in the subject's arterial blood.

9 Claims, 8 Drawing Sheets

(56) References Cited

U.S. PATENT DOCUMENTS

| | | | |
|---|---|---|---|
| 7,738,935 B1* | 6/2010 | Turcott ................ | A61B 5/0261 |
| | | | 600/336 |
| 2002/0111748 A1* | 8/2002 | Kobayashi ......... | A61B 5/14551 |
| | | | 702/31 |
| 2008/0208019 A1 | 8/2008 | Nitzan | |
| 2013/0053663 A1* | 2/2013 | Sivonen ............. | A61B 5/14551 |
| | | | 600/323 |
| 2019/0380655 A1* | 12/2019 | LeBoeuf ............ | A61B 5/02055 |
| 2021/0076953 A1* | 3/2021 | Huang .................. | G16H 50/30 |

OTHER PUBLICATIONS

The Extended European Search Report released by the European Patent Office on Feb. 17, 2026 for corresponding application No. 23771512.3; 8 pages.

* cited by examiner

1

GENERALIZED PULSE OXIMETRY METHOD FOR PERSONS OF ALL SKIN PIGMENTATIONS

TECHNICAL FIELD

The present invention generally relates to the quantification of the arterial blood oxygen saturation status of a living subject, severity of vasodilation from viral or bacterial infections, such as sepsis, the impact of pulmonary edema on blood oxygen saturation, severity of the resulting viral disease symptoms, volume overload, dehydration, hemorrhage and real time assessment of resuscitation of a living subject. More specifically, the present invention relates to systems and methods of using sensed external non-invasive indirect peripheral pulse optical plethysmograph (PPG) waveform measurements to assess in vivo functional and fractional blood oxygen saturation levels of living subjects irrespective of their skin pigmentation, from light skin pigmentation of white Caucasian origin, to skin rich in melanin pigments of sub-Saharan African origin.

BACKGROUND OF THE INVENTION

Conventional pulse oximetry methods of quantifying arterial blood oxygen saturation of a subject rely on transmission PPG waveforms over a finger or ear at two differing light wavelengths, typically red light at 660 nm and infrared light at 940 nm, and using an empirically derived relationship from healthy subjects of the ratio of ratios from the PPG waveforms at the two light wavelengths to quantify the subject's functional arterial blood oxygen saturation. Conventional pulse oximetry has an inherent skin pigmentation bias (references 1-3 below), leading to a significant overestimate of a subject's functional arterial blood oxygen saturation, especially at low oxygen saturation levels, on subjects with skin rich in melanin pigments. Conventional pulse oximetry significantly underestimates a subject's functional arterial blood oxygen saturation levels during severe vasodilation caused by viral or bacterial infections, such as sepsis, or from pulmonary edema, which can lead to unnecessary actions being taken on the subject.

The current disclosure herein improves upon conventional pulse oximetry by accurately determining the waveform of the red transmitted light as measured non-invasively an arterial optical plethysmograph waveform (PPG) using a pulse optical plethysmograph sensor over a finger, as a clip, or ear or other extremity, and thus remove the bias of skin pigmentation on the quantification of both functional and fractional arterial blood oxygen saturation assessment. The method utilizes an infrared long pass filter on the transmitted red waveform, thus providing an additional pulse oximetric ratio of ratios enabling the presence of methemoglobin to be quantified, and thus provide a more accurate assessment of both functional and fractional arterial blood oxygen saturation.

SUMMARY OF THE INVENTION

The present invention is an in vivo non-invasive method and apparatus for the measurement of the functional and fractional arterial blood oxygen saturation of a patient, by generalizing the pulse oximetry method to accommodate subjects of all skin pigmentations, and thus provide an accurate assessment of the subject's arterial blood oxygen saturation levels. The method requires an additional red light sensor with an infrared long pass filter to conventional pulse oximetry, and utilizes red and infrared light and sensors to non-invasively measure the peripheral pulse optical plethysmograph waveforms (PPG) at three light wavelengths, red, long pass red and infrared, positioned over a finger, or ear or other extremity, and from the pulse oximetric ratio of ratios transforms the PPG measurements by a processing device that determines the subject's arterial blood oxygen saturation directly, without the need for an empirical correction as is required in conventional pulse oximetry. The method determines the red transmitted light waveform and thus quantifies the wavelength shift from the incident red light due to the subject's skin pigmentation, and from in vivo hemoglobin extinction coefficients, determines the relative concentrations of oxygenated and deoxygenated hemoglobin and methemoglobin in the subject's arterial blood.

Other objects, features and advantages of the present invention will become apparent upon reviewing the following description of the preferred embodiments of the invention, when taken in conjunction with the drawings and the claims.

DETAILED DESCRIPTION OF THE DISCLOSED EMBODIMENT

Figure 1:
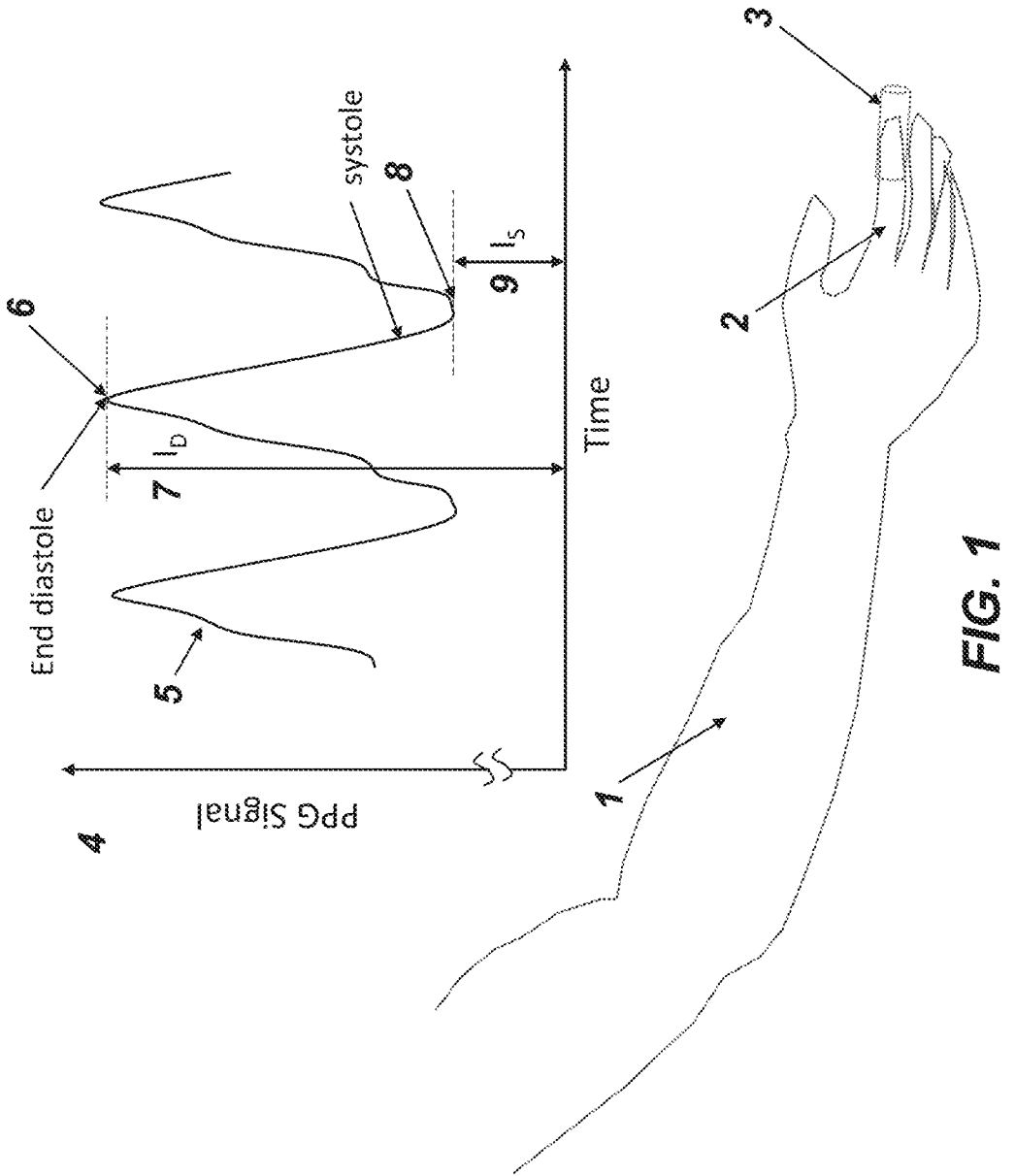
FIG. 1 is a schematic isometric view of an arm and associated method embodying principles of conventional pulse oximetry, to record the peripheral pulse optical plethysmograph waveform (PPG) from light transmitted through a finger for quantifying the arterial blood oxygen saturation status of the subject.

Several embodiments of the present invention are described below and illustrated in the accompanying drawings. The present invention is an improvement of conventional pulse oximetry to remove the skin pigmentation bias in the pulse oximetry assessment of arterial blood oxygen saturation and to quantify the presence of methemoglobin, thus determining both the functional and fractional arterial blood oxygen saturation levels of the subject. Conventional pulse oximetry requires non-invasive direct measurement of the peripheral pulse optical plethysmograph waveforms (PPG) by transmitted light, typically red at 660 nm and infrared at 940 nm, through a finger, or ear or other extremity, and from the PPG measurements the pulse oximetry ratio of ratios is determined as being the ratio of the arterial blood hemoglobin extinction functions for the two respective light wavelengths.

The hemoglobin molecules in the red blood cells transfer oxygen from the lungs to tissue cells by binding the oxygen to the ferrous heme group, with four molecules of oxygen per hemoglobin molecule. The hemoglobin affinity for oxygen is highly at higher oxygen partial pressures, and thus the hemoglobin releases the oxygen in the capillaries due to lower partial pressure. The hemoglobin molecules also transport nutrients, carbon dioxide, control systemic nitric oxide metabolism, redox regulation, blood rheology and viscosity. Hemoglobin molecules consists of two forms in which the iron in the heme group is in the ferrous state, oxygenated hemoglobin (HbO2) and deoxygenated hemoglobin (Hb). Another form of hemoglobin is methemoglobin (MetHb), in which iron in the heme group is ferric, and methemoglobin can't bind to oxygen but is essential to nitric oxide transport and its metabolism, to induce and control vasodilation. The enzyme, cytochrome b5 reductase, converts methemoglobin back to hemoglobin. Carboxyhemoglobin (COHb) is a stable form of carbon monoxide and hemoglobin formed when red blood cells are in contact with carbon monoxide.

Oxygen carrying capacity of blood depends on the cardiac output, i.e. blood flow, the concentration of hemoglobin in the blood, and the oxygen saturation of the hemoglobin. The functional form of oxygen saturation of blood, SO2, is the ratio of oxygenated hemoglobin concentration, HbO2, to HbO2 plus Hb, the deoxygenated hemoglobin. The fractional form of oxygen saturation of blood, fSO2, is the ratio of the oxygenated hemoglobin concentration, HbO2, to the total hemoglobin concentration, i.e. the sum of HbO2, Hb, MetHb and COHb. Arterial blood oxygen saturation, SaO2, typically varies in a healthy adult subject at sea level from 96-98%, with methemoglobin of 0% at rest to ~2% vasodilated, with partial oxygen pressure, PaO2, between 80 and 100 mmHg. Venous blood, the normal range of oxygen saturation is 70-80%, with oxygen partial pressure in the range of 40-50 mmHg. PaO2 and SaO2 both have major clinical and physiological significance, since they are dependent on the adequacy of respiratory function and are directly related to the oxygen supply to the organs. Both PaO2 and SaO2 can be obtained from a sample of arterial blood, with PaO2 determined by a blood gas analyzer, and SaO2 by co-oximetry, which uses the different light absorption spectra for oxygenated and deoxygenated hemoglobin. Non-invasive in vivo measurement of SaO2 can be determined by conventional transmission pulse oximetry, SpaO2, utilizing the different light absorption spectra for the various forms of hemoglobin, and improved as described herein, to correct for skin pigmentation bias, and the presence of methemoglobin.

Representatively illustrated in FIG. 1 is a system and associated method which embody principles of the present invention. The arm of the patient, 1, and digit finger 2 with a pulse oximeter device 3 positioned over the patient's digit finger, containing red and infrared light emitting diodes (leds) on the uppermost side of the digit finger, and with light intensity sensors on the opposite side of the digit finger to the leds, with both light sensors connected to the device 3. As shown by 4, the pulse optical plethysmograph waveforms 5 are measured for each light source and the end diastole peak 6 is recorded of magnitude 7 designated as ID, and the systole minimum 8 is recorded of intensity 9, designated as IS. Pulse oximetry is based on the isolation of the contribution of the arterial blood to light absorption by photoplethysmography (PPG), with measurement of light absorption changes from the cardiac-induced arterial blood volume changes. The PPG signal for light transmission through a finger is shown as 5 for a single light wavelength. The transmitted light intensity decreases during systole due to the increase in the arterial blood volume during systole, when blood is ejected from the left ventricle into the peripheral vascular system. The maximal and minimal values of the PPG signal ID and IS shown in FIG. 1 as 7 and 9, are proportional to the light irradiance transmitted through the tissue at end-diastole and at systole, when tissue blood volume is minimal and maximal, respectively.

The transmitted light intensity, It, through a tissue sample of width d that includes vessels with whole blood is given by, $$I_t = I_0 e^{-G - \epsilon C l} \tag{1}$$

where $I_0$ is the incident light intensity, G is the attenuation due to absorption and scattering in the tissue, and E is the extinction coefficient function, C is the concentration of the hemoglobin in the tissue, which is equal to the product of the concentration of the hemoglobin in the blood and the concentration of the blood in the tissue for the blood volume, and l is the effective optical path length, which is greater than d due to the effect of light scattering.

For small blood volume changes, ln(ID/IS) can be approximated by (ID-IS)/ID, so that:

$$\frac{I_D - I_S}{I_D} = \epsilon \Delta C l \tag{2}$$

equation (2) is the basis of difference pulse oximetry, with light transmission generally measured at two wavelengths, $\lambda_1$ and $\lambda_2$. The ratio of ratios R is defined by:

$$R = \frac{[(I_D - I_S)/I_D]_1}{[(I_D - I_S)/I_D]_2} \approx \frac{\epsilon_1}{\epsilon_2} \qquad (3)$$

assuming the difference in the blood concentration change $\Delta C$ between the two wavelengths can be neglected and that $l_1 \approx l_2$ for transmission PPG in the finger or earlobe, with the subscripts 1 and 2 referring to the two light wavelengths.

Figure 2:
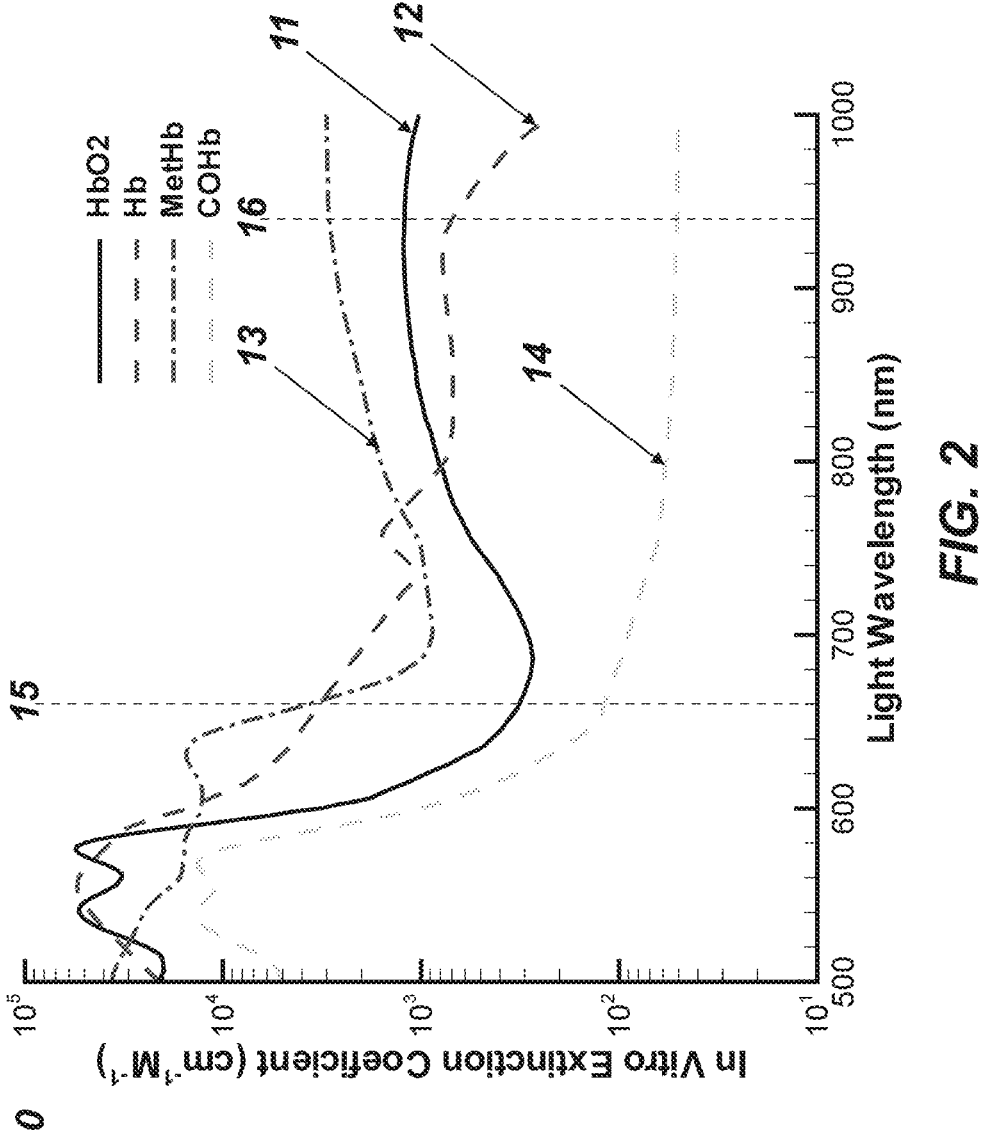
FIG. 2 is the plot of the in vitro hemoglobin extinction coefficients versus light wavelength and the two incident light wavelengths, red and infrared, typically used in conventional pulse oximetry to quantify the subject's arterial blood oxygen saturation levels.

Representatively illustrated in FIG. 2 is the plot 10 of the in vitro extinction coefficients of the various hemoglobin types as a function of light wavelength, being HbO2 designated as 11, Hb as 12, MetHb as 13 and COHb as 14. The typical two wavelengths selected for measurement in conventional pulse oximetry are shown as 15, 660 nm, and 16 in the infrared region, typically ~940 nm. The pulse oximetric ratio of ratios, R, in equation (3), is measured for the two incident wavelengths, 15 and 16. The extinction coefficients shown in 10 are in vitro determined, and their values are in error from in vivo values, due to differences in temperature, pH, red blood cell shape and deformability, etc. under the in vitro conditions which the extinction coefficients were measured. Also, the wavelengths of the incident light are not the same as the transmitted light, which leads to significant errors especially in the red light spectrum. Therefore, the relationship between the physiological parameter, SpaO2, pulse oximetry functional arterial blood oxygen saturation and the measured parameter, R, can't be derived directly.

Figure 3:
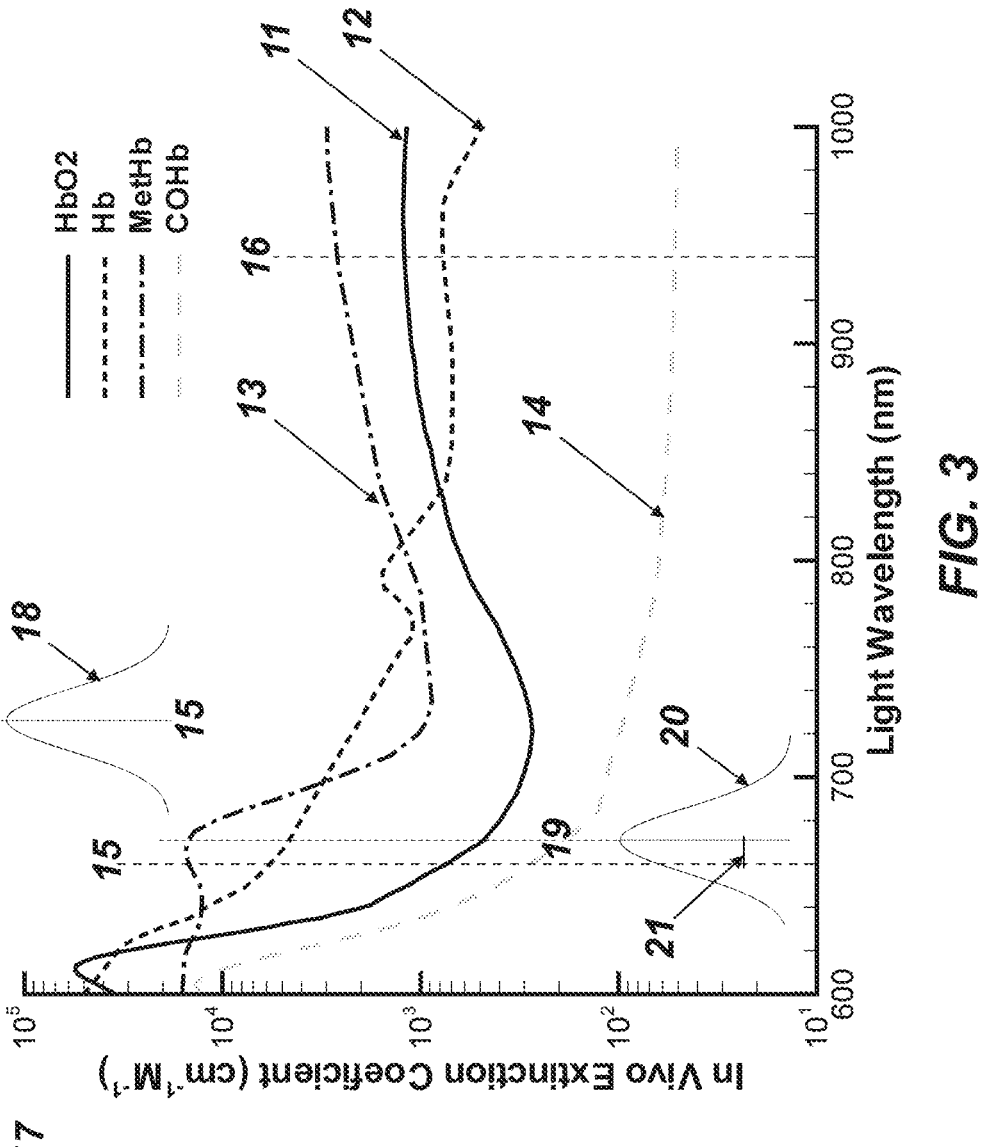
FIG. 3 is the plot of the in vivo hemoglobin extinction coefficients versus light wavelength and the two incident light wavelengths, red and infrared, used in the present invention, illustrating the need to quantify the transmitted red light wavelength shift from the incident red light due to the subject's skin pigmentation.

In conventional pulse oximetry, the relationship between R and SpaO2 is determined experimentally, with R measure in healthy volunteers with in vitro measurement of SaO2 in extracted arterial blood by means of co-oximetry. The formula relating R to SaO2 has been proposed as linear, with two unknown constants, or slightly non-linear by four unknown constants, with the constants determined by best-fit analysis. Empirical calibration is based on the assumption that the relationship between R and SaO2 is not influenced by intrasubject variability, which in the case of skin pigmentation variability is not the case, as skin pigmentation variability results in significant differences in R valves between subjects due to the variation of extinction coefficients in the red light spectrum, and thus leads to significant errors and skin pigmentation bias in the assessment of SpaO2.1-3 To determine SpaO2 directly from the measured R value, is shown in FIG. 3 a system and associated in vivo method which embodies principles of the present invention. The incident red light peak wavelength 15 and its normal distribution 18 are known, what is required is the need to determine the wavelength of the peak transmitted red light, 19 and its distribution 20, along with the in vivo extinction coefficients of the hemoglobin types with wavelength, especially in the red light spectrum wavelengths.

Figures 4A, 4B:
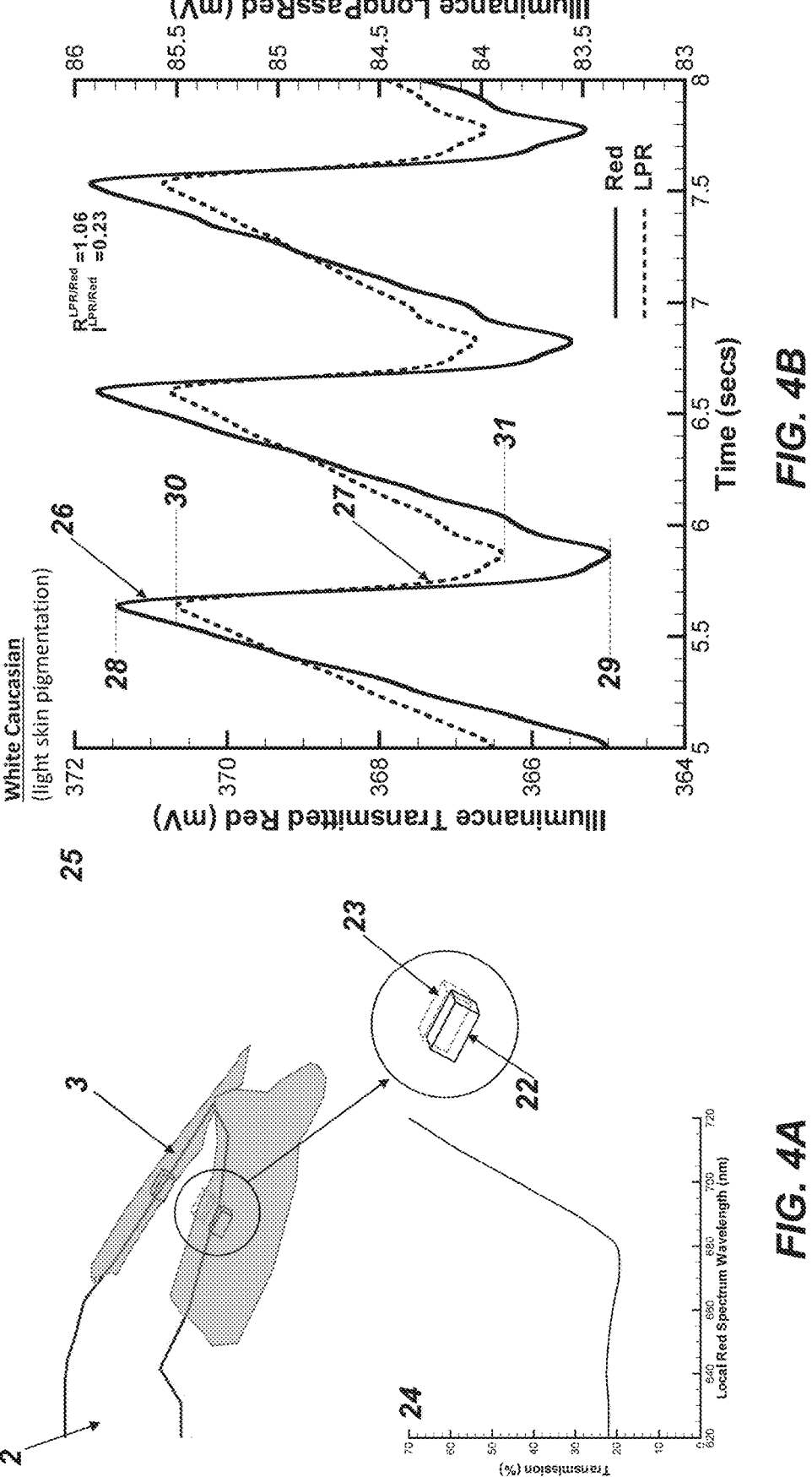
FIG. 4A is a schematic isometric view of a finger and associated method embodying principles of the present invention, using pulse optical plethysmograph sensors to non-invasively measure the peripheral pulse optical plethysmograph waveforms (PPG) of transmitted red, long pass red and infrared light for quantifying both the functional and fractional arterial blood oxygen saturation status of the subject.
FIG. 4B is a time history of the non-invasive direct peripheral pulse optical plethysmograph waveforms (PPG) recorded from the pulse optical plethysmograph sensors positioned over a finger of the transmitted red and long pass red light, to quantify their relative illuminance and pulse oximetric ratio of ratios for the subject.
Figure 5:
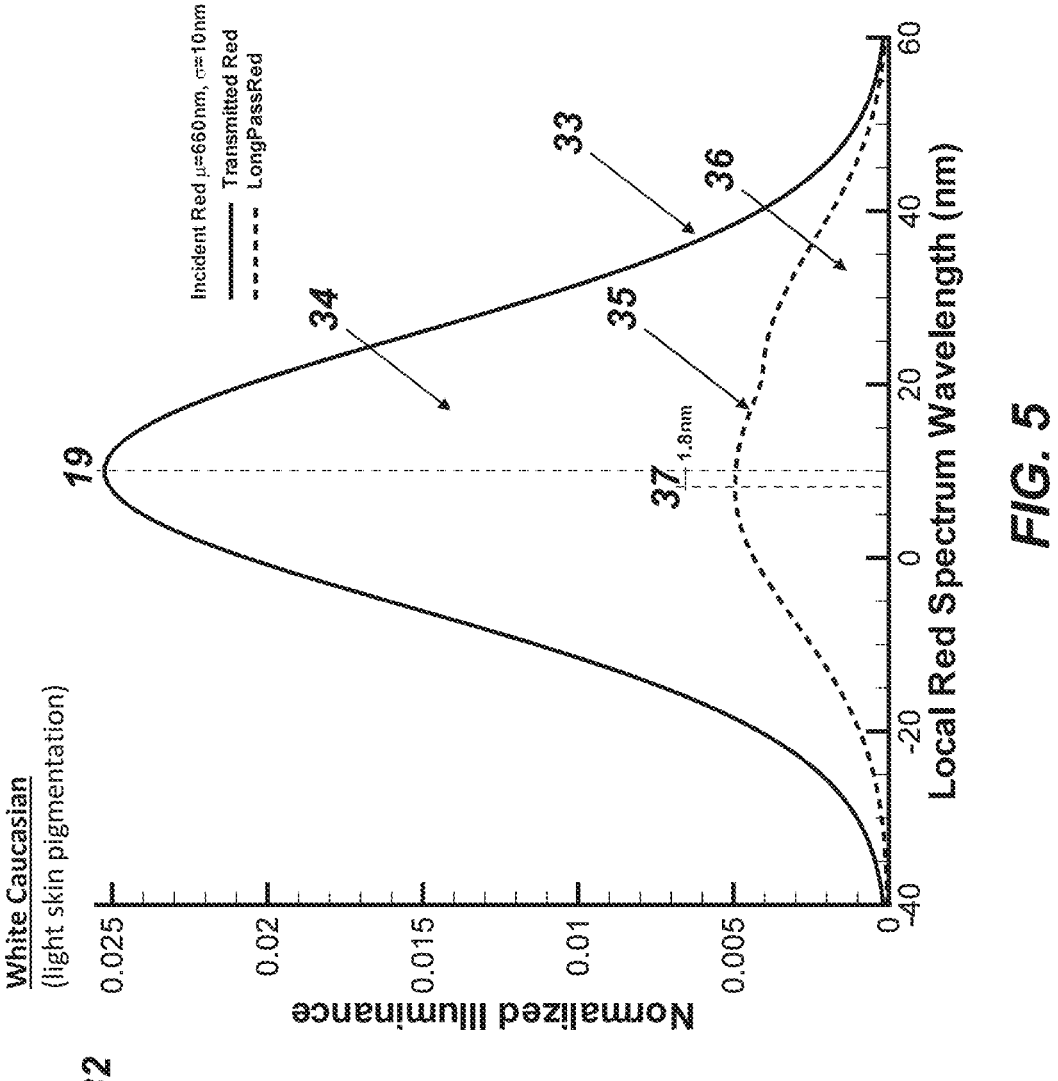
FIG. 5 is the constructed skewed normal distribution of the transmitted red light in the local red spectrum wavelength, for red light transmitted through the digit finger of a white Caucasian 5 male, along with the long pass red light distribution, for the PPG time history plots shown in FIG. 4B.

Representatively illustrated in FIG. 4A is a system and associated method which embody principles of the present invention. The digit finger of the subject is designated as 2, with a pulse oximeter 3 located on the subject's finger, with red and infrared light emitting diodes on one side of the finger and light sensors on the opposite side of the finger, similar to conventional pulse oximetry, but there are two red light sensors, 22 and 23, with the red light sensor 23 having an infrared long pass filter physically located over the sensor or incorporated into its light sensor chip. An example of a thin film infrared long pass filter used is shown as 24, with its transmission as a percentage plotted against wavelength for the red light wavelength spectrum. R values, given in equation (3) are measured for the three wavelengths, red, long pass red and infrared, utilizing only red and infrared light emitting diodes. Representatively illustrated in FIG. 4B are the PPG time history plots 25 for the red and long pass red PPG waveforms, 26 and 27 respectively, measured by the device 3 over a white Caucasian male digit finger. The ratio of ratios for red and infrared light for this subject, $$R_{IR}^{R},$$

was 0.52 for this subject. The maxima and minima of the PPG waveforms are designated as 28 and 29 for the transmitted red light, and 30 and 31 for the long pass red transmitted light. The R value for these two wavelengths, $$R_R^{LPR},$$

was determined to be 1.06 as shown in FIG. 4B, with an illuminance ratio of the two wavelengths, $$I_R^{LPR},$$

determined to be 0.23, also given in FIG. 4B. Knowing the incident red light distribution, as a normal distribution with peak intensity denoted at a wavelength of 15 and a normal distribution given by 18, with a mean of 660 nm and standard deviation of 10 nm, the infrared long pass filter transmission function, 24, and the illuminance ratio of the two wavelengths, $$I_R^{LPR},$$

the skewed normal distribution of the long pass transmitted red light can be determined, as shown by 32 in FIG. 5 with normalized illuminance plotted against local red light wavelength spectrum, with 0 being a wavelength of 660 nm. The wavelength of the peak transmitted red light intensity is denoted as 19, at a local wavelength of 10 nm, with its skewed normal distribution denoted by 33 and an illuminance of unity, 34, the area under the transmitted red light intensity versus wavelength. The transmitted long pass red light distribution is given by 35, with an illuminance, i.e. area under the PPG plot, designated as 36, being equal to 0.23, to give a wavelength shift to the left of 1.8 nm from the transmitted red light peak, 19, for the peak intensity of the long pass transmitted red light 35, being denoted as 37, 1.8 nm shifted left of the peak transmitted red light intensity 19.

The extinction function ratios for the red, long pass red and infrared light can be derived from the in vivo extinction coefficients of each of the three hemoglobin, HbO2, Hb and metHb, and their respective concentrations CO, CD and CM, with CD=(1−CO−CM) as given by equations (4) and (5), resulting in two equations and two unknowns, CO and CM, since the nine (9) in vivo extinction coefficients are known.

$$C_O \varepsilon_O^R + (1 - C_O - C_M)\varepsilon_D^R + C_M \varepsilon_M^R = R_{IR}^R \in {}^{IR} \qquad (4)$$

$$C_O \varepsilon_O^{LPR} + (1 - C_O - C_M)\varepsilon_D^{LPR} + C_M \varepsilon_M^{LPR} = R_R^{LPR} \in {}^R \qquad (5)$$

with $\in {}^{IR}$, $\in {}^R$, $\in {}^{LPR}$ the infrared, red and long pass red extinction functions respectively, and $$\varepsilon_O^R, \varepsilon_D^R, \varepsilon_M^R$$

are the extinction coefficients of oxygenated, deoxygenated and methemoglobin at the red wavelength and similarly for the infrared and long pass red wavelengths.

Figure 6:
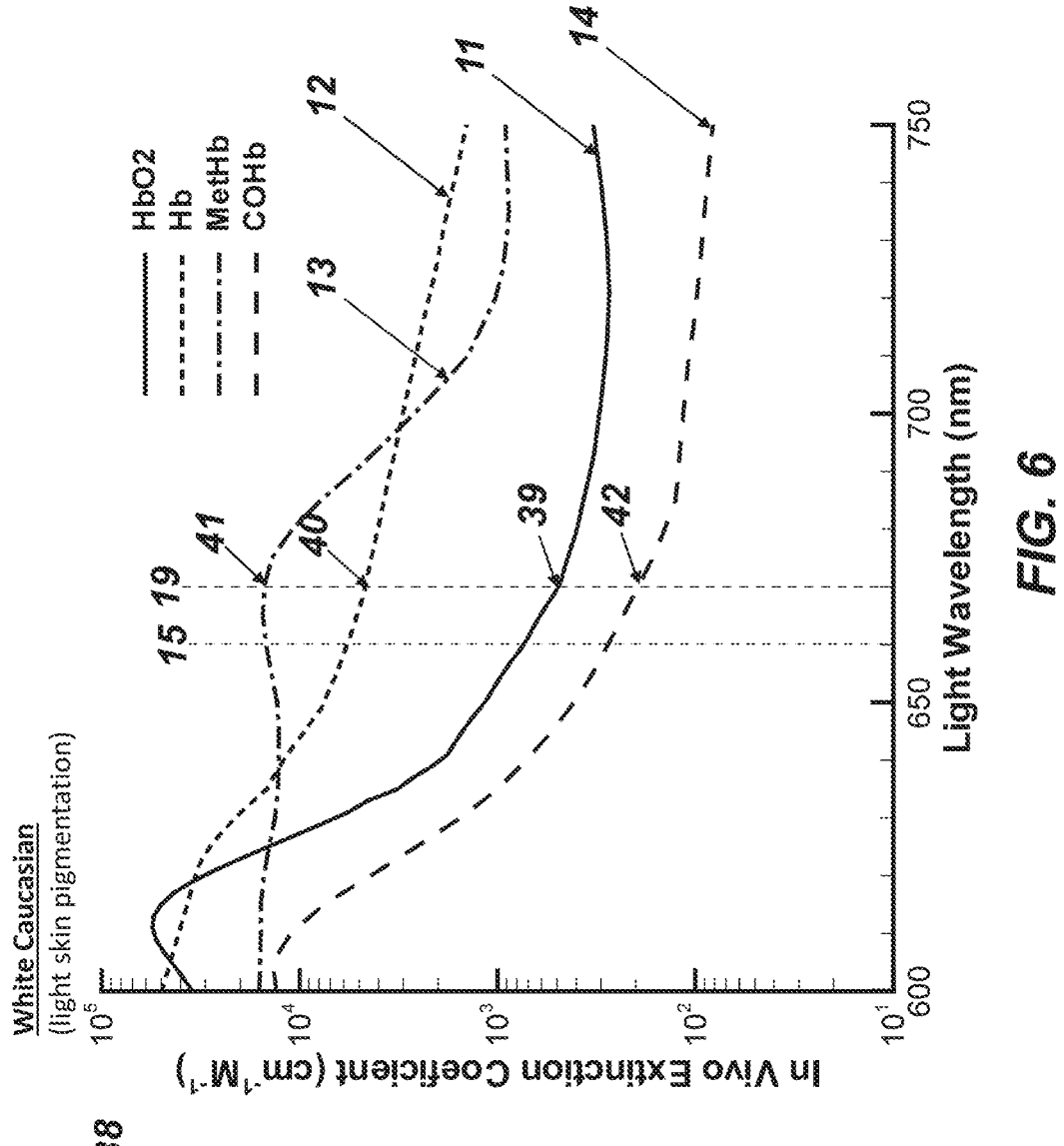
FIG. 6 is the plot of the in vivo hemoglobin extinction coefficients versus light wavelength in the red light spectrum, for incident red light of 660 nm and the transmitted red light with peak intensity at 670 nm, transmitted through the digit finger of a white Caucasian male, used in the present invention, to determine both the functional and fractional arterial blood oxygenation status of the subject, independent of the subject's skin pigmentation.

Representatively illustrated in FIG. 6 is a system and associated method which embody principles of the present invention, being the in vivo extinction coefficients in the red light spectrum denoted as 38, knowing the wavelength of the peak intensity of the transmitted red light, 19, in this case of a white Caucasian male of 670 nm, the extinction coefficients for the red transmitted light for this subject can be found, as denoted by 39, 40, 41 and 42 for HbO2, Hb, MetHb and COHb respectively, and similarly for the long pass red transmitted light with the wavelength of its peak intensity 37 being 1.8 nm left shifted from the transmitted red light wavelength 19. Since the in vivo extinction coefficients as a function of wavelength in the infrared region are near flat lying, the extinction coefficients in this region can be assumed to be the same as those at the incident infrared light wavelength, 16. A conventional pulse oximeter measured a SpaO2=97% on the above white Caucasian male, as did the generalized method described here, as CO=97%, CD=3% and CM=0%. Immediately after a sauna, the white Caucasian male measured SpaO2=91% on a conventional pulse oximeter, while for the generalized method described here, ratios measured immediately after the sauna were $$R_{IR}^R = 0.76, \ R_R^{LPR} = 1.1, \text{ and } I_R^{LPR} = 0.28$$

to yield CO=95%, CD=3% and CM=2%, with a functional oxygen saturation SpaO2=97% both before and after the sauna, and a fractional oxygen saturation fSpaO2=97% before the sauna, and fSpaO2=95% after the sauna, illustrating the inaccuracies that can be introduced by just considering functional oxygen saturation. So for this subject, conventional pulse oximetry underestimated the functional oxygen saturation by 6 percentage points after a sauna, which induced a moderate amount of vasodilation in the subject; however, extreme vasodilation induced by a viral or bacterial infection such as sepsis, would have generated considerable more methemoglobin, resulting in extreme errors in the functional oxygen saturation of the subject by conventional pulse oximetry.

In the method described above, the second red light sensor fitted with an infrared long pass filter could be replaced by a chirped photodiode or chirped phototransistor.

Similar to method described above, of a second red light sensor fitted with an infrared long pass filter, a third red light sensor fitted with a short pass filter could provide the four (4) wavelength measurements of the R's, the ratio of ratios, to provide three equations similar to equations (4) and (5), for the transmitted red, short pass red, long pass red and infrared enabling CC, the concentration of COHb to be determined, as described earlier for CO, CD and CM.

Figure 7:
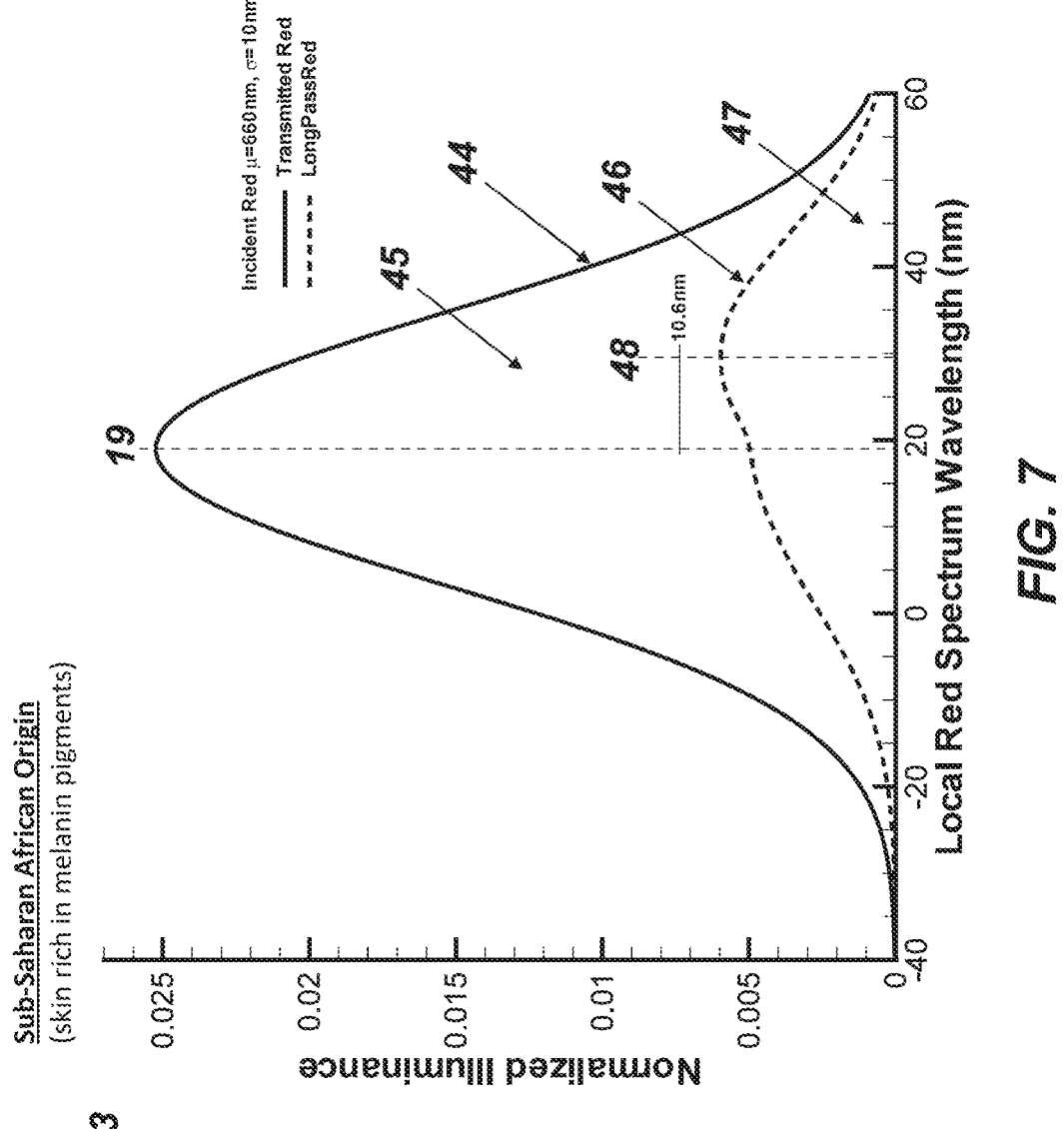
FIG. 7 is the constructed skewed normal distribution of the transmitted red light in the local red spectrum wavelength, for red light transmitted through the digit finger of a male of sub-Saharan African origin, along with the long pass red light distribution.

The PPG time history waveforms for red, long pass red and infrared were measured by the device 3 over a sub-Saharan African origin male subject's male digit finger. The subject had a skin pigmentation rich in melanin pigments. The ratio of ratios for red and infrared light for this subject, $$R_{IR}^R,$$

was 0.43 for this subject. The R value for the red and long pass red wavelengths, $$R_R^{LPR},$$

was 0.85, with an illuminance ratio of the two wavelengths, $$I_R^{LPR},$$

determined to be 0.265. Knowing the incident red light distribution, as a normal distribution with peak intensity denoted at a wavelength of 15 and a normal distribution given by 18, with a mean of 660 nm and standard deviation of 10 nm, the infrared long pass filter transmission function, 24, and the illuminance ratio of the two wavelengths, $$I_R^{LPR},$$

the skewed normal distribution of the long pass transmitted red light can be determined, as shown by 43 in FIG. 7 with normalized illuminance plotted against local red light wavelength spectrum, with 0 being a wavelength of 660 nm. The wavelength of the peak transmitted red light intensity is denoted as 19, at a local wavelength of 19 nm, with its skewed normal distribution denoted by 44 and an illuminance of unity, 45, the area under the transmitted red light intensity versus wavelength. The transmitted long pass red light distribution is given by 46, with an illuminance, i.e. area under the PPG plot, designated as 47, being equal to 0.265, to give a wavelength shift to the right of 10.6 nm from the transmitted red light peak, 19, for the peak intensity of the long pass transmitted red light 46, being denoted as 48, 10.6 nm shifted right of the peak transmitted red light intensity 19.

Figure 8:
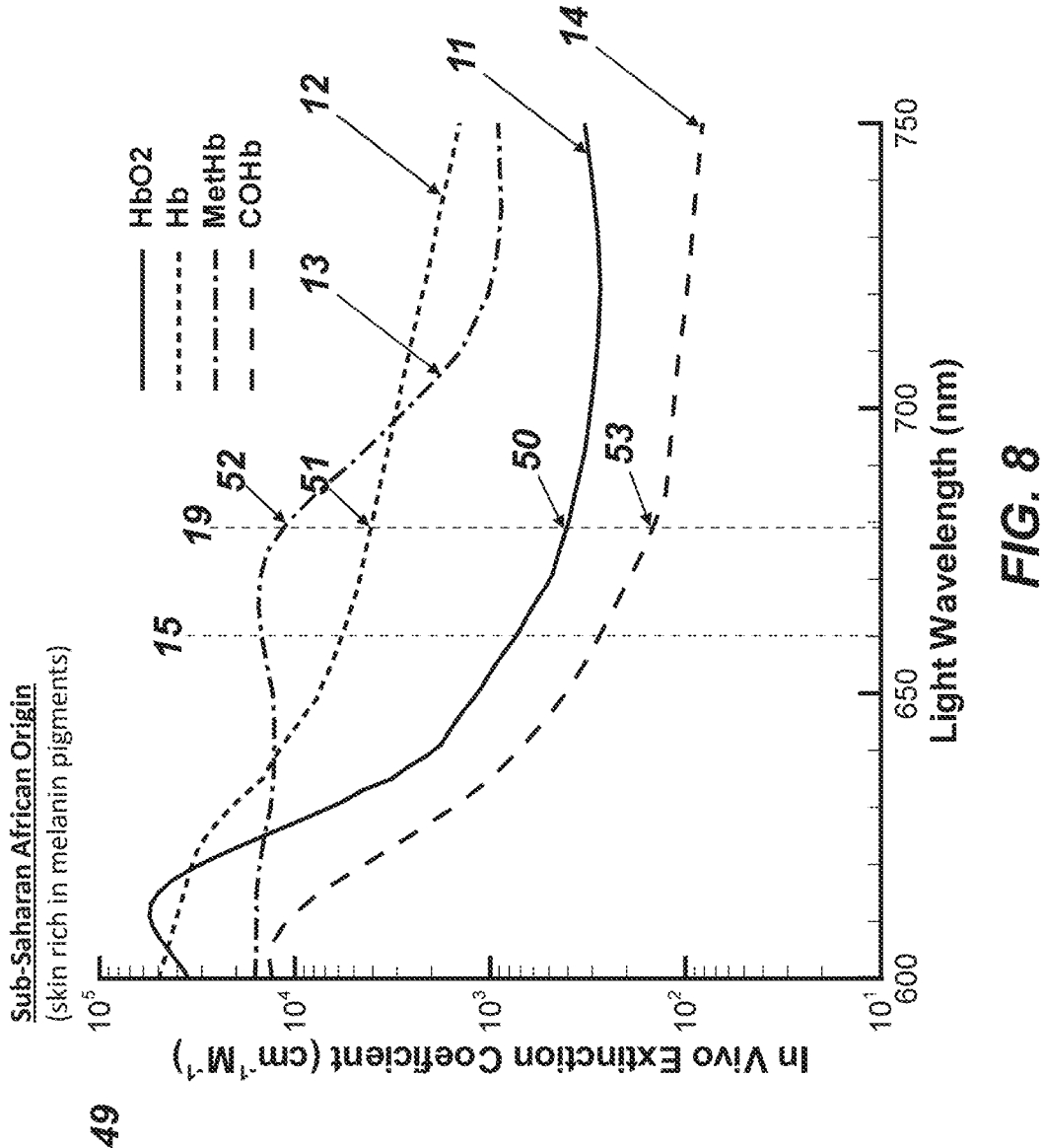
FIG. 8 is the plot of the in vivo hemoglobin extinction coefficients versus light wavelength in the red light spectrum, for incident red light of 660 nm and the transmitted red light with peak intensity at 679 nm, transmitted through the digit finger of a male of sub-Saharan African origin, used in the present invention, to determine both the functional and fractional arterial blood oxygenation status of the subject, independent of the subject's skin pigmentation.

Representatively illustrated in FIG. 8 is a system and associated method which embody principles of the present invention, being the in vivo extinction coefficients in the red light spectrum denoted as 49, knowing the wavelength of the peak intensity of the transmitted red light, 19, in this case of a sub-Saharan African origin male with skin rich in melanin pigments being 679 nm, the extinction coefficients for the red transmitted light for this subject can be found, as denoted by 50, 51, 52 and 53 for HbO2, Hb, MetHb and COHb respectively, and similarly for the long pass red transmitted light with the wavelength of its peak intensity 48 being 10.6 nm right shifted from the transmitted red light wavelength 19. Since the in vivo extinction coefficients as a function of wavelength in the infrared region are near flat lying, the extinction coefficients in this region can be assumed to be the same as those at the incident infrared light wavelength, 16. A conventional pulse oximeter measured a SpaO2=99.3% on the above sub-Saharan African origin male with skin rich in melanin pigments, while the generalized method described here, yielded hemoglobin concentrations of CO=97%, CD=3% and CM=0%. Conventional pulse oximetry overestimated functional oxygen saturation by two (2) percentage points for this subject, and as 5 detailed in the literature (1-3), conventional pulse oximetry overestimates functional oxygen saturation by at least six (6) percentage points at low functional oxygen saturations of ~86% in subjects of skin rich in melanin pigments. As detailed earlier for the white Caucasian male, conventional pulse oximetry has significant errors in oxygen saturation estimates in the cases of a subject undergoing vasodilation, either from exercise, temperature induced in a sauna, or viral or bacterial infection induced such as in sepsis, and such errors are also present in subjects with skin rich in melanin pigments.

Finally, it will be understood that the preferred embodiment has been disclosed by way of example, and that other modifications may occur to those skilled in the art without departing from the scope and spirit of the appended claims.

REFERENCES

1. Sjoding, M W, Dickson, R P, Iwashyna T J, Gay S E, Valley T S 2021. Racial Bias in Pulse Oximetry Measurement, n engl j med 383; 25 nejm.org Dec. 17, 2020.
2. Moran-Thomas A. How a popular medical device encodes racial bias. Boston Review. Aug. 5, 2020.
3. Bickler P E, Feiner J R, Severinghaus J W. Effects of skin pigmentation on pulse oximeter accuracy at low saturation. Anesthesiology 2005; 102: 715-9.

What is claimed is:

1. A method of quantifying the arterial blood oxygen saturation status and hemoglobin concentrations of a patient in near real time, the method comprising the steps of:

a) Place a transmission pulse optical plethysmograph device on a patient;

b) Determine the maxima and minima of the optical plethysmograph waveforms over a cardiac cycle for red, long pass red and infrared light wavelengths, wherein the long pass red wavelength results from filtering the red light waveform with a long pass red filter;

c) Determine the ratios of extinction functions for the three light wavelengths and the illuminance ratio of the long pass red to red waveforms, to quantify the wavelength of the peak intensity of the transmitted red and long pass red light;

d) Determine the in vivo extinction coefficients of oxygenated, deoxygenated and methemoglobin molecules for the three transmitted wavelengths, and compute the concentrations of these three hemoglobin molecules in the arterial blood; and e) Display the arterial blood oxygen saturation status and hemoglobin concentrations of the patient.

2. The method of claim 1, wherein the device is a red and infra-red pulse optical plethysmograph sensor with an additional red light sensor fitted with an infrared long pass filter.

3. The method of claim 2, wherein the device is a red and infra-red pulse optical plethysmograph sensor with the additional red light sensor being a chirped photodiode or chirped phototransistor.

4. The method of claim 1, wherein the pulse optical plethysmograph sensor has a motion piezoelectric sensor attached.

5. The method of claim 4, wherein the pulse optical plethysmograph waveforms PPG are collected only when the motion piezoelectric sensor is below threshold motion criteria.

6. The method of claim 1, wherein the constructed transmitted red light waveform is of a skewed normal distribution.

7. The method of claim 1, wherein the device is a red and infra-red pulse optical plethysmograph sensor with a second red light sensor fitted with an infrared long pass filter, a third red light sensor fitted with a short pass filter to provide four (4) wavelength measurements of the ratio of ratios, determine the in vivo extinction coefficients of oxygenated, deoxygenated, methemoglobin and carboxyhemoglobin molecules for the four transmitted wavelengths, and compute the concentrations of these four hemoglobin molecules in the arterial blood.

8. The method of claim 7, wherein the device is a red and infra-red pulse optical plethysmograph sensor with the additional red light sensors being chirped photodiodes or chirped phototransistors.

9. A pulse oximeter comprising:

a) a red light emitting diode or transistor for emitting a red light and an infrared light emitting diode or transistor for admitting and infrared light, the red light emitting diode or transistor and the infrared light emitting diode or transistor mounted adjacent to one side of a patient's finger or earlobe;

b) an infrared light sensor mounted on a second side of the patient's finger or earlobe, for receiving the infrared light, and producing an infrared light waveform;

c) a first red light sensor mounted on the second side of the patient's finger or earlobe, for receiving the red light, and producing a red light waveform; and d) a second red light sensor mounted on the second side of the patient's finger or earlobe, the second red light sensor having a long pass red input filter located over the second red light sensor for producing a long pass red waveform in response to red light passing through the long pass red light filter, wherein the infrared light waveform, the red light waveform, and the long pass red waveform represent data that is accurate for patients with varying pigmentation.

\* \* \* \* \*